(12) United States Patent
Takiguchi et al.

(10) Patent No.: US 7,491,496 B2
(45) Date of Patent: Feb. 17, 2009

(54) METHOD FOR IMMOBILIZING NUCLEIC ACID AND METHOD FOR MANUFACTURING BIOSENSOR USING THE SAME METHOD

(75) Inventors: Hiroshi Takiguchi, Suwa (JP); Hitoshi Fukushima, Suwa (JP)

(73) Assignee: Seiko Epson Corporation, Tokyo (JP)

( * ) Notice: Subject to any disclaimer, the term of this patent is extended or adjusted under 35 U.S.C. 154(b) by 49 days.

(21) Appl. No.: 11/090,238

(22) Filed: Mar. 28, 2005

(65) Prior Publication Data

US 2005/0221362 A1    Oct. 6, 2005

(30) Foreign Application Priority Data

Apr. 1, 2004    (JP)    ............... 2004-109363

(51) Int. Cl.
*C12Q 1/68* (2006.01)
*C12M 1/00* (2006.01)

(52) U.S. Cl. ........................ 435/6; 435/283.1
(58) Field of Classification Search ........... None
See application file for complete search history.

(56) References Cited

U.S. PATENT DOCUMENTS

| | | | | |
|---|---|---|---|---|
| 5,705,628 | A | * | 1/1998 | Hawkins .................. 536/25.4 |
| 6,287,776 | B1 | * | 9/2001 | Hefti ............................. 435/6 |
| 6,506,564 | B1 | * | 1/2003 | Mirkin et al. ................. 435/6 |
| 7,056,664 | B1 | * | 6/2006 | Hartwich et al. ............. 435/6 |
| 2002/0068304 | A1 | * | 6/2002 | Urry .......................... 435/7.1 |

FOREIGN PATENT DOCUMENTS

| | | |
|---|---|---|
| JP | A-2004-003913 | 1/2004 |
| JP | A-2004-525607 | 8/2004 |
| WO | WO 0031101 A1 * | 6/2000 |
| WO | WO 0031101 A1 * | 6/2000 |
| WO | WO 02/18643 A3 | 3/2002 |
| WO | WO 03/018854 A2 | 3/2003 |

OTHER PUBLICATIONS

Rehn et al. (IEEE-NANO 2004, Fourth IEEE Conference on Nanotechnology, Muenchen, Germany, Aug. 16-19, 2004, 532-534).*
Peterson et al. ("The effect of surface probe density on DNA hybridization" Nucleic Acids Res. Dec. 15, 2001;29(24):5163-8).*
Petrovykh et al. ("Quantitative analysis and characterization of DNA immobilized on gold" J Am Chem Soc. Apr. 30, 2003;125(17):5219-26).*
Zhang et al. ("Effects of Ionic Strength and Counterion Valency on Adsorption of Hydrophobically Modified Polyelectrolytes" Macro. 1996; 29:7299-7301).*
Steel et al. (Electrochemical quantitation of DNA immobilized on gold. Anal Chem. Nov. 15, 1998;70(22):4670-7).*
Tonya M. Herne et al.; "Characterization of DNA Probes Immobilization on Gold Surfaces"; Journal of the American Chemical Society, 119; pp. 8916-8920; 1997.
Alexander W. Peterson et al.; "The effect of surface proved density on DNA hybridization"; Nucleic Acids Research, vol. 29, No. 24; pp. 5163-5168; 2001.
T. Herne et al., "Characterization of DNA Probes Immobilized on Gold Surfaces," J. Am. Chem. Soc. 1997, 119, pp. 8916-8920.

* cited by examiner

*Primary Examiner*—Kenneth R. Horlick
*Assistant Examiner*—Christopher M. Babic
(74) *Attorney, Agent, or Firm*—Oliff & Berridge, PLC (57) ABSTRACT

A method is provided to enable high-density absorption when immobilizing nucleic acid probes onto a solid support surface by suppressing electrostatic repulsion among the nucleic acids. A nucleic acid immobilization method to immobilize a nucleic acid onto a solid support, includes: preparing a solution containing a probe molecule which includes a nucleic acid, a spacer molecule, and at least one kind of a divalent cation; and contacting the solution with the solid support for incubation.

13 Claims, 6 Drawing Sheets

METHOD FOR IMMOBILIZING NUCLEIC ACID AND METHOD FOR MANUFACTURING BIOSENSOR USING THE SAME METHOD

BACKGROUND

Exemplary aspects of the present invention relate to a method to immobilize nucleic acids, a method to manufacture a biosensor using this method, and a method to detect nucleic acids.

A biosensor is being used to detect a target molecule in a sample by taking advantage of unique interactions of biorelated molecules, such as enzyme-substrate reaction, antigen-antibody reaction, and hybridization of nucleic acids in basic research, blood test and genetic analysis in the field of medicine, process control in food industry, and environmental measurement.

The biosensor includes a biorelated substance as a sensing part that reacts uniquely with a target substance and a converter which converts changes caused by interactions between the target substance and the sensing part into physical signals, such as electric current or voltage. Accordingly, in order to make a highly sensitive biosensor, it is necessary to optimize the sensing part structure and a reading device to read the signals.

One way to immobilize nucleic acids as the sensing part of the biosensor is to form a thin film containing nucleic acids on a surface of a solid support, such as a substrate. In order to form the thin film, a linker is put between ends of the nucleic acid molecules in advance to bond with specific groups so that the molecules are absorbed onto the surface of the solid support. The specific group is a thiol group, for example. By first forming a gold thin film on the solid support surface, a self-assembled monolayer (SAM) of a nucleic acid probe is formed on the solid support surface through gold-sulfur bond. Thus, the sensor on which a DNA probe, having a well-known base sequence, is immobilized and which detects hybridization of this probe with the nucleic acids contained in the sample by using physio-chemical signals (e.g., volume of fluorescence) is now in practical use.

The efficiency in the hybridization of the target nucleic acid contained in the sample with the DNA probe immobilized on the biosensor largely depends on densities of the DNA probes (See Peterson, A. W. et al., Nucleic Acids Research, vol. 29, No. 24, 5163-5168 (2001)). In order to enhance sensitivity of the DNA sensor, it is necessary to maximize the densities of evenly dispersed DNA probes while maintaining distance between the probes as required for hybridization. To control the immobilizing DNA probes so as to have optimal densities, a method in which a relatively low-volume molecule called a spacer molecule is suitably inserted between the nucleic acid probes is employed, for example. There is a report on an experiment in that the probe is a single-stranded DNA with a thiolated end and that 6-mercapto-1-hexanole is used as the spacer molecule (See Tonya M. Herne et al., Journal of the American Chemical Society, 119, pp. 8916-8920 (1997)).

One of the methods generally employed upon using the spacer molecules is a method in which the DNA probes are first absorbed onto the substrate and, thereafter, the spacer molecules are embedded therein. Another such method is coabsorption in that a mixed solution of the DNA probes and spacer molecules is immobilized in one step. Mainly employed at present is the former. However, the process to form the film through various steps requires a relatively long time, and fine adjustment of the densities of the DNA probes is not without difficulties.

With the coadsorption method, it is possible to save process time because this film formation is performed by one step. At the initial stage, by merely adjusting composition ratios of various kinds of molecules including the DNA probes in the solution at the initial stage, it is logically possible to adjust the densities of the nucleic acid probes on the biosensor by using the method in that the solid support is immersed in this mixed solution and that the volumes of the molecules absorbed on the solid substrate are adjusted by altering mixing ratios of these molecules.

SUMMARY

However, because DNA contains phosphoric acids in its backbone and is thus negatively charged, electrostatic repulsion among DNAs creates a certain distance among them, preventing them from getting any closer. Therefore, even when using the coabsorption method as described above, the adjustment of the composition ratio of the DNA probes and spacer molecules does not always reflect on the DNA probe densities, and it may be difficult to create an optimal distance.

To increase the absorption densities of the DNA probes, it is effective to add cations, such as sodium ion in a form of salt, into the solution. The presence of cations in the solution suppresses the electrostatic repulsion among the backbone radicals, enabling DNA probes to have high densities. It can be calculated that the distance among the DNA probes created due to electric charge to be, for example, 2 nm at 20 mM NaCl concentration (Debye screening length). However, in reality, because DNA has a flexible, macromolecular structure and makes revolving movement, the distance cannot be any smaller than some tens of nanometers.

In an attempt to further shorten the distance among the DNA probes, the repulsion of DNA must be suppressed by increasing the sodium ion concentration. For example, to shorten the distance caused by the charge up to around 0.3 nm, the sodium ion concentration needs to be raised up to 1M, which is not easy to realize.

Accordingly, exemplary aspects of the present invention aims to provide a method to enable high-density absorption when immobilizing nucleic acid probes onto the solid support surface by suppressing the electrostatic repulsion among nucleic acids. By suppressing the repulsion among nucleic acids, it becomes easy to control the absorption densities by adjusting the concentration ratios and to obtain the optimal absorption density when carrying out the coabsorption method using the solution containing the spacer molecules and nucleic acid probe molecules.

Upon series of vigorous researches in view of the above issues, the present inventors have accomplished the present invention, with discoveries that the nucleic acid probe molecules can be absorbed at a very high density by adding a divalent metal cation to the solution containing the nucleic acid probe molecules and spacer molecules when carrying out the coabsorption, and that, by using the divalent cation, the above-described effect can be obtained at a concentration much lower than that when using a sodium ion, which is a monovalent cation.

Exemplary aspects of the present invention relate to: (1) A nucleic acid immobilization method to immobilize a nucleic acid onto a solid support, including: preparing a solution containing a probe molecule having a nucleic acid, a spacer molecule, and at least one kind of a divalent cation; and contacting the solution with the solid support for incubation; (2) The method as described in (1), the divalent cation being either a magnesium ion or a calcium ion; (3) The method as described in (1) or (2), the solution containing the divalent cation at a total density of 0.1 mM-100 mM; (4) The method as described in any one of (1) through (3), the solution further containing a monovalent cation or a salt thereof at a total density of 10 mM-2 M; (5) The method as described in (4), the monovalent cation being a sodium ion; (6) The method as described in any one of (1) through (5), each nucleic acid molecule may be modified and being a polynucleotide or an oligonucleotide composed of a single-stranded DNA, RNA, or PNA; (7) The method as described in any one of (1) through (6), the probe molecule including a thiol group; (8) The method as described in any one of (1) through (7), the spacer molecule being either a 6-mercapto-1-hexanole or a polyethylene glycol at whose one end a thiol group is introduced; (9) The method as described in (7) or (8), a gold thin film being formed at a region on the solid support surface where the probe molecule or the spacer molecule is absorbed; (10) A method for manufacturing a biosensor having a nucleic acid probe as a sensing part, including using the method to immobilize the nucleic acid as described in any one of (1) through (9); (11) A method to detect a target nucleic acid molecule in a sample, including: contacting the biosensor manufactured by the method according to (10) with the sample for incubation; and detecting whether or not a hybridized nucleic acid is present in the nucleic acid probe of the biosensor; (12) The method as described in (11) to detect DNA, RNA, or a single nucleotide polymorphism thereof.

Exemplary aspects of the present invention enable high-density immobilization by suppressing the repulsion among the nucleic acids caused by electric charge of their own when immobilizing the nucleic acid molecules, such as DNA to the solid support by absorption.

According to an exemplary aspect of the present invention, when coabsorbing the nucleic acid probes and spacer molecules, the absorption densities of the two can be readily controlled by adjusting the concentration ratios of the spacer molecules and nucleic acid probes in the solution.

DETAILED DESCRIPTION OF EXEMPLARY EMBODIMENTS

In the following, terms used in the present specification will be explained in detail based on working examples.

The nucleic acid immobilization method of an exemplary aspect of the present invention is characterized in that at least one kind of divalent cation or the salt thereof is added to the solution containing the probe molecules and spacer molecules. As the divalent cation, a metal ion, such as magnesium ion ($Mg^{2+}$), calcium ion ($Ca^{2+}$), strontium ion ($Sr^{2+}$), and barium ion ($Ba^{2+}$) can be used. Among them, magnesium ion or calcium ion are easy to treat. To this solution, only one kind of these divalent cations may be added, or two or more kinds may be added. By adding the divalent cations, the electrostatic repulsion among the negatively charged nucleic acids can be suppressed and the probe molecules can be immobilized at a high density.

The salt of the divalent metal cation can be first used to make a highly concentrated aqueous solution, which can be then diluted and added to the solution containing the probe molecules and spacer molecules. As the salt, water-soluble chloride, such as $MgCl_2$ or $CaCl_2$ may be used but is not limited thereto.

In the nucleic acid immobilization method of an exemplary aspect of the present invention, these divalent cations to be added to the solution containing the probe molecules and spacer molecules may be 0.1 mM-100 mM, preferably, 0.1 mM-20 mM, or, more preferably, 0.1 mM-10 mM. Although the sodium ion, which is a monovalent cation, produced no effect until about some 10 mM-1 M was added, the divalent cation produced a satisfactory effect at lower concentrations.

In contrast, in the nucleic acid immobilization method of an exemplary aspect of the present invention, by adding the monovalent cation or the salt thereof, together with the divalent cation, to the solution containing the probe molecules and spacer molecules, it becomes possible to finely adjust the suppression of the electrostatic repulsion among the nucleic acids. The monovalent cation may be sodium ion (Na+) or potassium ion (K+), for example, and the salt thereof may be a chloride thereof, such as sodium chloride or potassium chloride, respectively. As described above, because the monovalent cation produces no effect unless it is relatively highly concentrated, addition of 10 mM-2 M of the monovalent cation, preferably 20 mM-1.5 M, or more preferably 100 mM-about 1 M enables the fine adjustment.

The probe molecules used in an exemplary aspect of the present invention contains nucleic acids and are such that can be immobilized onto the solid support. The nucleic acids means such nucleic acids that either some or all of which may be modified (or substituted), that are also single- or double-stranded oligonucleotides or polynucleotides, and that may be single-stranded oligonucleotides or polyclonal antibody nucleotides, with some or all of which being possibly modified (or substituted). Specifically, the nucleic acids are those chosen from DNA, RNA, PNA (peptide nucleic acids), CNA (cyclohexylanyl nucleic acid), HNA (hexytol nucleic acids), p-RNA (pyranosyl-RNA), oligonucleotides made of the above-mentioned nucleic acid molecules, polynucleotides made of the above-mentioned nucleic acid molecules, and the like, but may be from DNA, RNA, and PNA.

The spacer molecules used in an exemplary aspect of the present invention: can be mixed with the nucleic acid molecules to make the solution; do not interfere with functions of the probe molecules immobilized on the solid support surface; are not particularly limited to any spacer molecules so long as they are of low molecule substance that does not affect the operation as the biosensor; and can be chosen suitably by those skilled in the art depending on a desired density of the nucleic acids on the biosensor, the structure of the probe molecule, and the solid support used.

The "spacer molecules" mentioned above is a compound or the salt thereof expressed as X-A-B, where X is a functional group that can be immobilized onto the solid support; A is an alkylene group or polyethylene glycol group (PEG) that may have a substituent of $C_{1-15}$; and B is either a hydroxyl group, amino group, ferrocenyl group, or a carboxyl group. Preferably, B is a hydroxyl group, and A is an alkylene group or a polyethylene glycol group of $C_6$.

The probe molecule and spacer molecule used in an exemplary aspect of the present invention have, at each end, the functional group that can be immobilized onto the solid support. Examples of such functional group are a thiol group, disulfide group, sulfide group, carboxyl group, amino group, isocyanate group, chloride group, epoxy group, carbodiimide group, and maleimide group. Among them, a thiol group is preferable. By introducing the thiol group in advance to the ends of the "probe molecule" and "spacer molecule," and by using the solid support on which the gold thin film and the like are formed on its surface, the probe molecules and spacer molecules form the SAM on the solid support and are easily immobilized.

Accordingly, the spacer molecule used in an exemplary aspect of the present invention may be a thiol compound having a hydroxyl group or a polyethylene glycol into whose one end a thiol group is introduced, for example. Specifically, alkanethiol where A is an alkylene group, or PEG thiol where X is a thiol group and A is PEG is particularly preferable. Among them, 6-mercapto-1-hexanole (MCH) expressed as $HS-(CH_2)_6-OH$ is most preferable.

The "solid support" used in an exemplary aspect of the present invention can be of any form or material as long as it does not interfere with the immobilization of the nucleic acids of the probe molecules and spacer molecules. It may be on a substrate or may take a form of a particle, string, tape, or film, for example. Among them, substrate is suitable for detection and handling purposes. The material and thickness of the substrate can be appropriately chosen by those skilled in the art depending, for example, on kinds of the functional groups that contribute to absorption of the probe molecules for immobilization and on the signal detection device employed to detect the target nucleic acid molecules. The material for the substrate may be chosen preferably from glass, metal (e.g., gold, silver, copper, aluminum, platinum, aluminum oxide, $SrTiO_3$, $LaO_3$, $NdGaO_3$, $ZrO_2$), silicon (e.g., silicon oxide), and polymer resin (e.g., polyethylene terephthalate, polycarbonate).

On the region on the "solid support" used in an exemplary aspect of the present invention where the probe molecules are absorbed, a metal thin film (preferably of gold, silver, copper, or platinum), for example, may be formed. The gold thin film itself can be formed by any suitable method or the corresponding methods thereof, such as electroplating, electroless plating, sputtering, vapor deposition, or ion plating. By using the solid support on which the metal thin film is formed, the probe molecules and spacer molecules having the thiol group at the ends can form the SAM on the substrate surface.

Further, the surface of the "solid support" used in an exemplary aspect of the present invention may be coated with a macromolecule compound or a silane-coupling agent and be introduced with a highly reactive functional group. Examples of such a functional group are an amino group, carboxyl group, disulfide group, epoxy group, carbodiimide group, and a maleimide group. For example, when the probe molecule and spacer molecule have the thiol group, they are covalently bonded to the maleimide group on the substrate surface, and when they have the amino group, the probe molecule and spacer molecule become immobilized as they are covalently bonded with the epoxy group on the substrate surface.

The probe molecules and spacer molecules used in the nucleic acid immobilization method of an exemplary aspect of the present invention are first prepared as a mixed solution including the two before being subject to the absorption reaction with the solid support. The probe molecules and spacer molecules in the solution normally have a total concentration of 0.1-5 µM, and, only within this range of concentration the solid support surface can be properly coated with the probe molecules. A preferable total concentration is 0.1-10 µM, more preferably 0.1-2 µM, and even more preferably 0.5-about 1 µM.

The composition ratio (mol %) of the probe molecules and spacer molecules or the salt thereof in this mixed solution is not limited to any particular ratio, and those skilled in the art may choose an appropriate ratio depending on the desired density of the nucleic acids on the biosensor, the structure of the probe molecules, the spacer molecules used, and the type of solid support used. Any composition ratio depending on the purpose is possible as long as the mixed solution containing the probe molecules and spacer molecules has the composition ratio within the range of: probe molecules/spacer molecules=about 1 mol %/about 99 mol % 1–about 99 mol %/about 1 mol %.

According to the nucleic acid immobilization method of an exemplary aspect of the present invention, the situation where the probe molecules repulse each other to create distance among them can be avoided. Thus, the mixing ratio of the probe molecules and spacer molecules in the solution readily reflects on the ratio of the absorption to the solid support. The mixing and composition can be finely adjusted within any of the ranges of: nucleic acid molecules/spacer molecules=about 1/99-about 10/90, about 10/90-about 20/80, about 20/80-about 30/70, about 30/70-about 40/60, about 40/60-about 50/50, about 50/50-about 60/40, about 70/30-about 80/20, about 80/20-about 90/10, about 90/10-about 99/1 (concentration ratio, mol %), and the coating over the solid substrate can be accomplished.

The solvent for the solution containing the probe molecules, spacer molecules, and at least one kind of the divalent cations used in an exemplary aspect of the present invention is not limited to any particular solvent as long as it dissolves both probe molecules and spacer molecules and does not interfere with the absorption reaction at the solid substrate surface. Examples of such solvent are, various kinds of phosphoric acid buffers, such as PBS (50 mM $KPO_4$, 5 mM EDTA, 1M NaCl, pH7.0) and TE buffer (a mixed buffer of Tris-HCl and EDTA, pH8.0). pH of these buffers is commonly around pH5.5-8.5 or, preferably, around pH7-8 but is not particularly limited thereto.

The above-described solution containing the probe molecules, spacer molecules, and at least one kind of divalent cations can itself be arranged according to any suitable methods or methods corresponding thereto and can be prepared, for example, by arranging each solution of the probe molecules, spacer molecules, and cations and mixing them at appropriate ratios.

In the nucleic acid immobilization method of an exemplary aspect of the present invention, the probe molecules and spacer molecules are immobilized onto the solid support surface by contacting the above-described solution containing the probe molecules, spacer molecules, and at least one kind of divalent cations with the above-described solid support for incubation.

Upon immobilization, if the solid support surface is polluted with organic substances in the air, for example, it is desirable to use organic solvent, strong acid when necessary, or ozone generated by ultraviolet radiation in order to rinse, discompose, and remove the polluted substances off the solid support before use. One suitable method is to rinse the metal surface in boiled organic solvent (e.g., acetone), followed by rinsing using a UV ozone rinsing machine, while another rinsing method is to use a piranha solution (a mixed solution of: hydrogen peroxide/concentrated sulfuric acid=30/70).

In the nucleic acid immobilization method of an exemplary aspect of the present invention, the reaction temperature when the solution and the solid support surface are contacted for incubation is commonly 0-40° C., preferably around 20-35° C. but not particularly limited thereto. The reaction time sufficient for incubation is commonly 10 min-24 h or, more preferably, 10 min-12 h but is not particularly limited thereto.

Exemplary aspects of the present invention further provides a method to manufacture the biosensor using the nucleic acid immobilization method of an exemplary aspect of the present invention and a method to detect the target nucleic acid molecules using this biosensor. Explanations on the terms and various conditions already used to describe the nucleic acid immobilization method of an exemplary aspect of the present invention will be omitted here in describing the biosensor manufacturing method and the nucleic molecule detection method.

The method to manufacture the biosensor of an exemplary aspects of the present invention include: preparing a solution containing a probe molecule, a single-stranded nucleic acid having thiol group as a terminal end, and 6-mercapto-1-hexanol as the spacer molecule, and a magnesium ion or a calcium ion; and contacting this solution with the solid support substance on whose surface a gold thin film is formed. By this method, the surface of the solid support is coated with the probe molecules and spacer molecules mixed in the solution in accordance with the mixing ratio, without having the probe molecules to repulse with each other.

The biosensor manufactured by the biosensor manufacturing method of an exemplary aspect of the present invention is a biosensor having, per 1 $cm^2$, at least $1\times10^8-1\times10^{16}$ nucleic molecules or, preferably, at least $1\times10^{11}-1\times10^{14}$ nucleic molecules.

The nucleic acid molecule detection method of an exemplary aspect of the present invention means a method to determine the presence or non-presence of the target molecules by detecting whether or not the target nucleic acid molecules contained in the sample were hybridized with the nucleic acids of the probe molecules by use of the biosensor manufactured by the nucleic acid immobilization method or the biosensor manufacturing method of an exemplary aspect of the present invention. This detection method is useful to detect, in particular, oligonucleotide or polynucleotide of DNA (including cDNA), oligonucleotide or polynucleotide of RNA (such as mRNA), single nucleotide polymorphisms (SNPs) of these nucleic acids, or the like.

When immobilizing the molecules containing double-stranded nucleic acids as the probe molecules, they are to be treated with heat or denatured by chemicals so as to change to single-stranded before being contacted with the sample so that the hybridization with the target nucleic acid molecules takes place.

For the detection of the hybridization, a method to detect changes in emission intensity upon labeling the target nucleic acid molecules with fluorescence or the like is common. Although a method that does not use labels, such as surface plasmon resonance (SPR) or quartz crystal microbalance (QCM) may be used, it is not limited thereto. Those skilled in the art can carry out the detection of hybridization by choosing the most suitable method, reagent, device, and so forth.

The following working examples of exemplary aspects of the present invention are illustrative, and the present invention is not to be limited thereto. Those skilled in the art can carry out the present invention to the maximum extent by giving various alterations to the following working examples, and the alterations thus made are to be included in the exemplary aspects of the present invention.

(1) Preparation of Mixed Solution

As the probe molecule, a nucleic acid probe by the expression dA20-$(CH_2)_6$—SH was purchased. Here, dA20 means deoxyadenosine 5'-phosphoric acid.

As the spacer molecule, a compound by the expression HO—$(CH_2)_6$—SH (hereinafter "MCH") was purchased.

Working examples 1 through 3, in which the divalent cation were added to the solutions, and comparative examples 1 and 2, in which the divalent cations were not added were conducted. Table 1 shows the ions added for each example.

TABLE 1

|  | Working Example 1 | Working Example 2 | Working Example 3 | Comparative Example 1 | Comparative Example 2 |
| --- | --- | --- | --- | --- | --- |
| Divalent Cation | $MgCl_2$ (10 mM) | $MgCl_2$ (10 mM) | $CaCl_2$ (10 mM) | — | — |
| Monovalent Cation | — | NaCl (1 M) | NaCl (1 M) | — | NaCl (1 M) |

As the solvent, phosphoric acid buffer (50 mM $KPO_4$, pH7.0) was used to dissolve 0.5 μM each of nucleic probes and MCH as well as the divalent and monovalent cations at concentrations shown in Table 1.

(2) Coabsorption of Probe Molecules and Spacer Molecules

The immobilization of the probe molecules and spacer molecules as well as the hybridization of the target nucleic acid with the immobilized probe molecules were measured by QCM.

Specifically, as the solid support, a probe provided with a gold electrode used for QCM measurement was used. The probe was immersed in the solution prepared in the above step (1) to absorb the probe molecules and spacer molecules. With the absorption of these molecules, there occurs a change in the number of vibrations by the thin film formed on the gold electrode, and by detecting this change, the absorbed molecules can be quantitatively detected. Further, when the target nucleic acid molecules are hybridized with the probe molecules, a change in the quantity can be detected also as the change in the number of vibrations, and, thereby the hybridization can be quantitatively detected.

Figure 1:
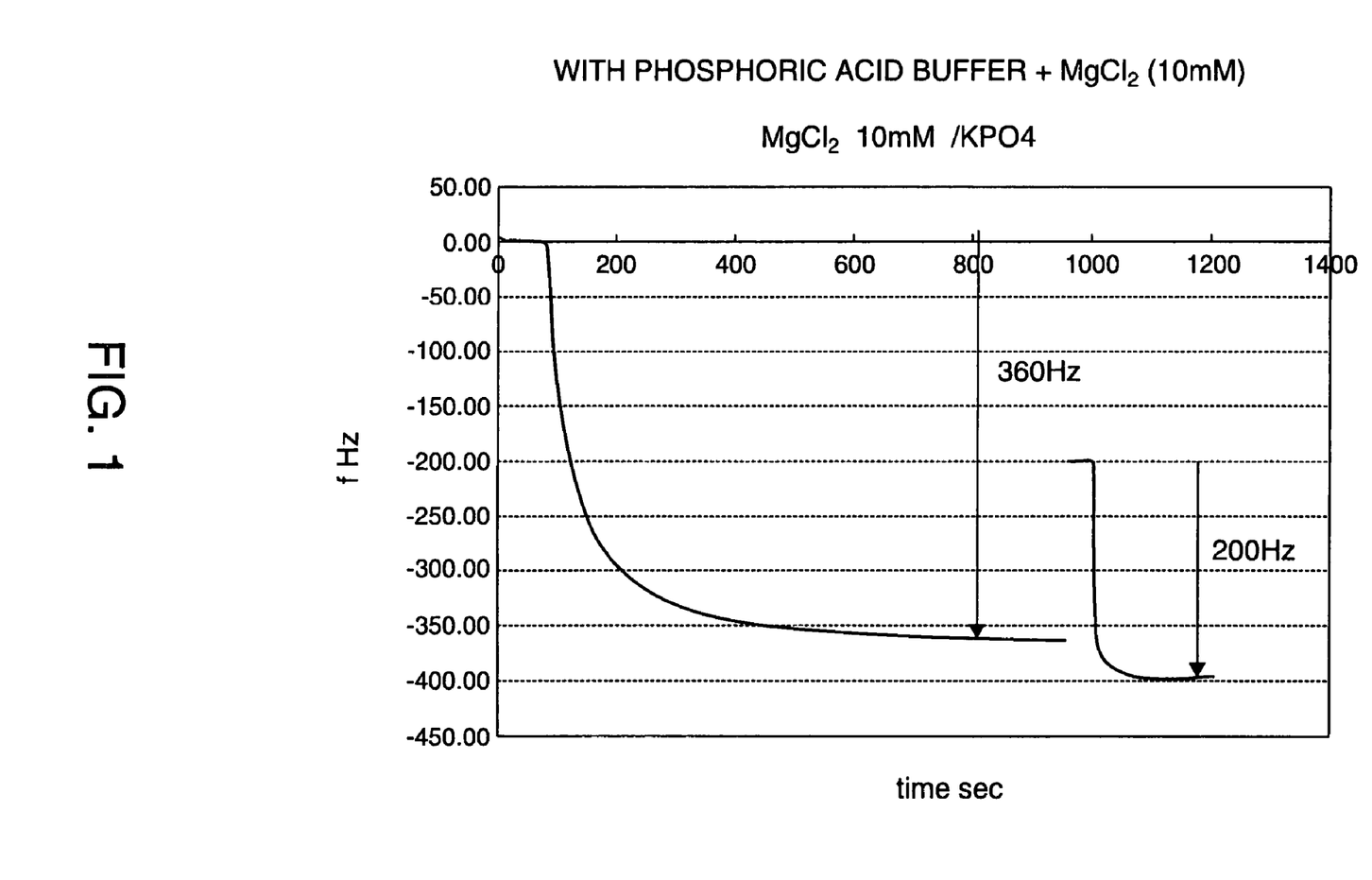
FIG. 1 shows results of QCM measurements when 10 mM $Mg^{2+}$ was added.
Figure 2:
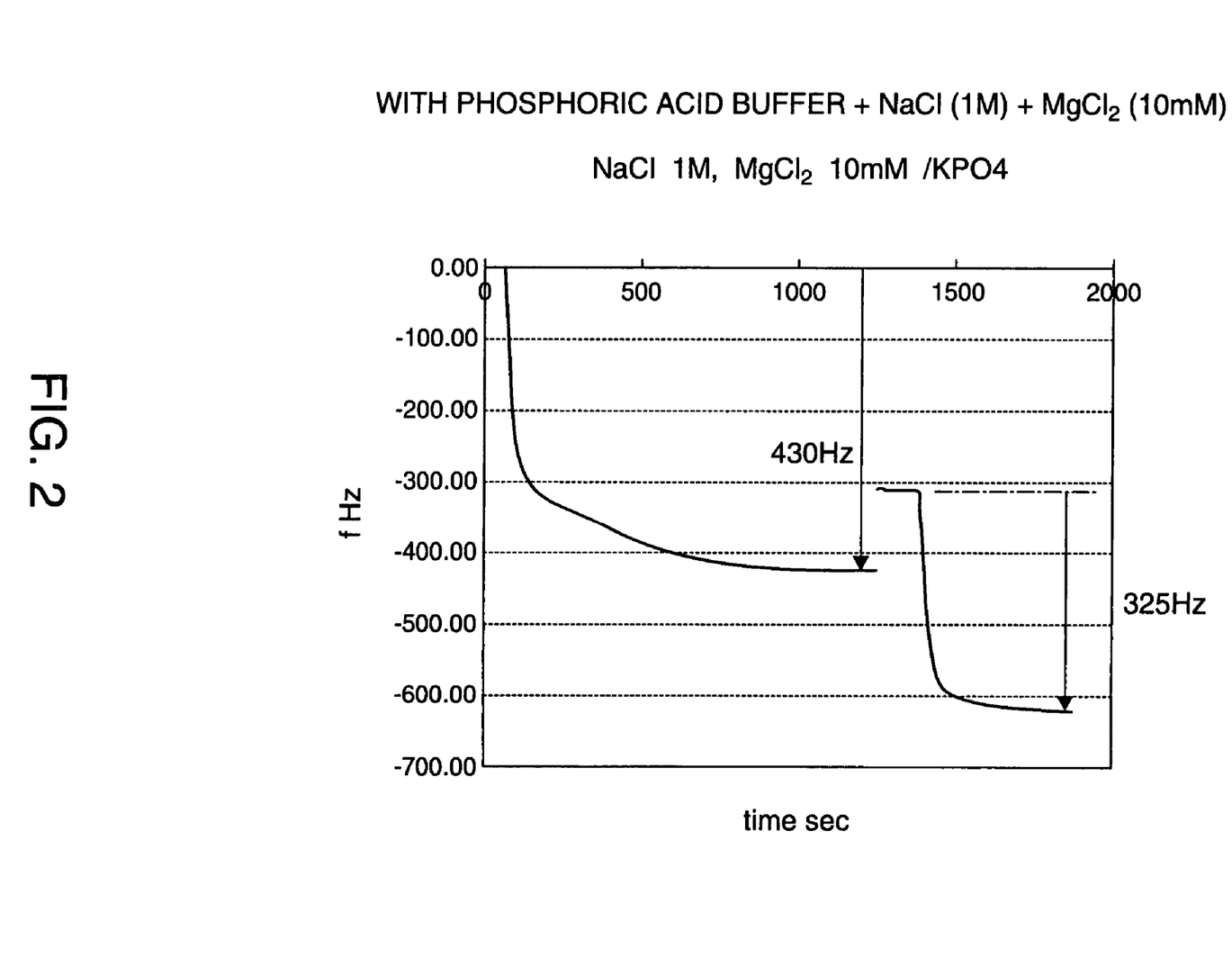
FIG. 2 shows results of QCM measurements when 10 mM $Mg^{2+}$ and 1M $Na^+$ were added.
Figure 3:
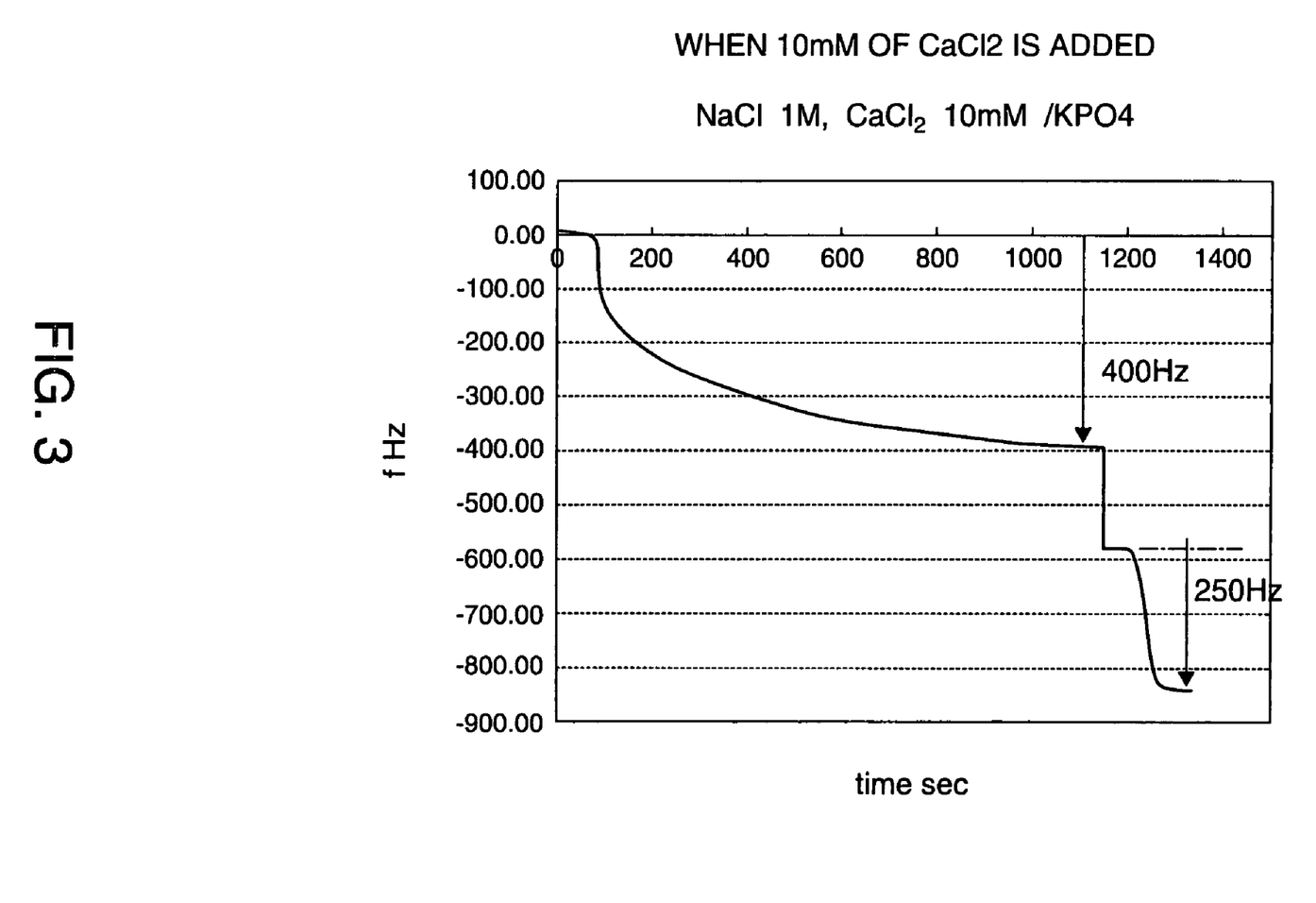
FIG. 3 shows results of QCM measurements when 10 mM $Ca^{2+}$ and 1 M $Na^+$ were added.
Figure 4:
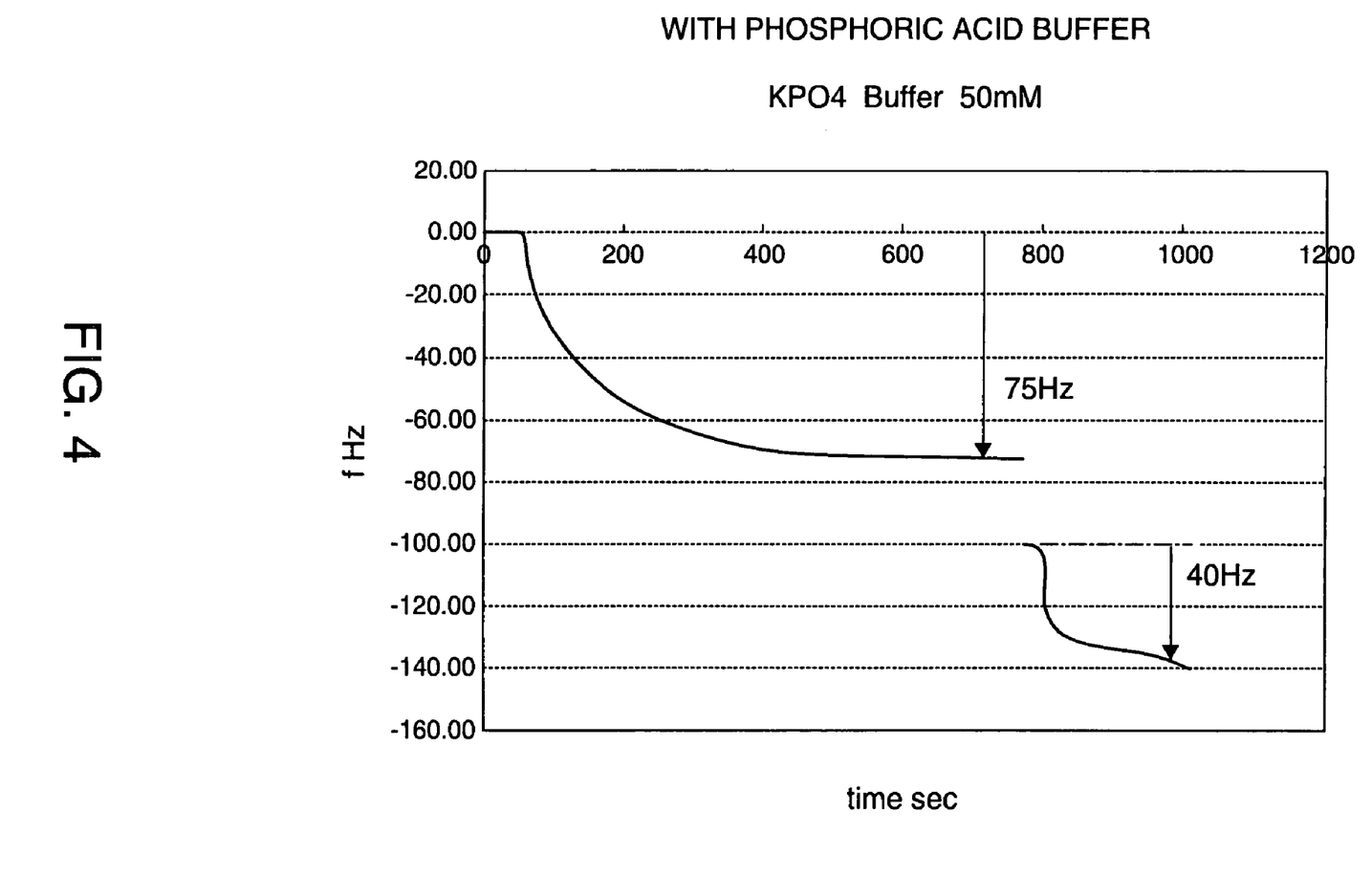
FIG. 4 shows results of QCM measurements when 1 M $Na^+$ was added.
Figure 5:
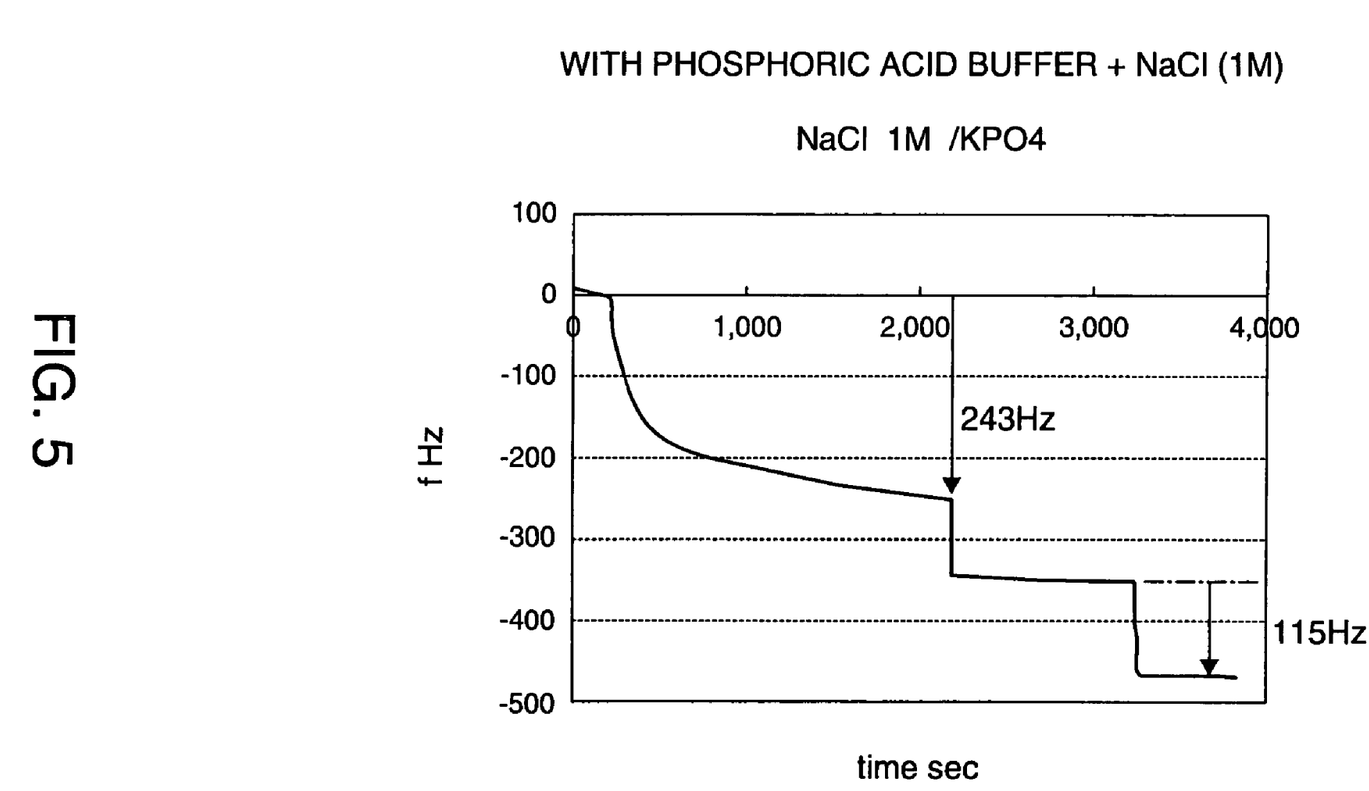
FIG. 5 shows results of QCM measurements when no cation was added.
Figure 6:
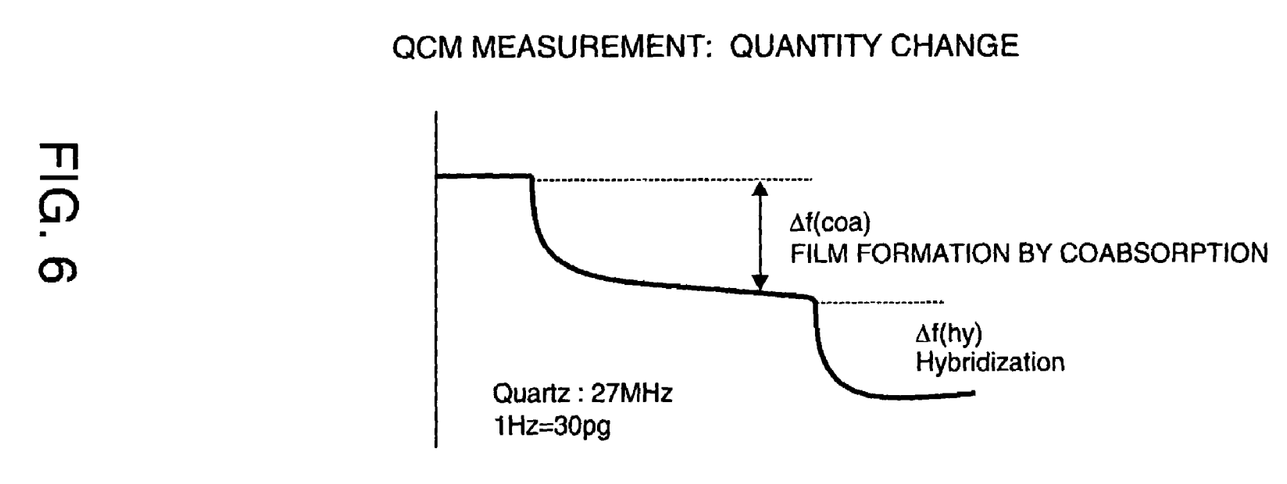
FIG. 6 is a graph illustrating how to determine results of the QCM measurements.

FIG. 6 shows an example of a graph obtained by QCM measurement. The vertical axis indicates the number of vibrations by the thin film. The horizontal axis indicates the time elapsed. The number of vibrations decreases at first upon coabsorption of the probe molecules and spacer molecules. The amount of this decrease (Δf(coa)) indicates the volume of the film containing the probe molecules and spacer molecules formed by coabsorption. Then, by hybridizing the target nucleic acids with the nucleic acid portion of the probe molecules, the number of vibrations by the thin films further decreases. The amount of this decrease (Δf(hy)) indicates the relative amount of hybridization.

Table 2 shows averages of Δf(coa) in the working examples and comparative examples 1 and 2.

TABLE 2

|  | Working Example 1 | Working Example 2 | Working Example 3 | Comparative Example 1 | Comparative Example 2 |
| --- | --- | --- | --- | --- | --- |
| Δf (coa) [Hz] | 360 | 430 | 400 | 75 | 243 |
| Ratio to Comparative Example 1 (times) | 4.80 | 5.73 | 5.33 | 1.00 | 3.24 |

Compared to the comparative example 1 in which the cations were not added, the comparative example 2, in which only the monovalent cations (1 M $Na^+$) were added, showed an increase in Δf(coa) more than three times that in the comparative example 1, while, there was nearly five times of an increase in the working example 1 in which only the divalent cations (10 mM $Mg^{2+}$) were added. Although the divalent cations were at a low concentration of 10 mM compared to the monovalent cations at a high concentration of 1 M and, an effect was produced in that the amount of coabsorption greatly increased.

Also, in the working example 2 where both the divalent cations (10 mM $Mg^{2+}$) and the monovalent cations (1 M $Na^+$) were added, Δf(coa) increased by 70 Hz compared to the working example 1 in which only the divalent cations were added. It was thus ensured that the amount of absorption could be adjusted by using the divalent cations combined with the monovalent cations.

Further, it was found from the working example 3 that the effect by the divalent cations could not only be produced by use of $Mg^{2+}$ but be produced also by use of $Ca^{2+}$.

(3) Hybridization

Because Δf(coa) expresses a total number of changes in the number of vibrations corresponding to the amount of probe molecule absorption and in the number of vibrations corresponding to the amount of spacer molecule absorption, it does not ensure that the probe molecules became highly dense. Therefore, a decrease in the number of vibrations due to hybridization of the probe molecules with the target nucleic acids was next measured, and the changes in the densities of the probe molecules were observed.

For the solution to be used for hybridization, the solvent containing 1 M of the above-mentioned phosphoric acid buffer NaCl was used to dissolve 1 μM of (dT)20 as DNA molecules complementary to the nucleic acid portions of the probe molecules. Into this solution, the probe to which the probe molecules and spacer molecules had been coabsorbed was immersed for incubation.

Table 3 shows averages of Δf (hy) in the working examples 1—3 and comparative examples 1 and 2.

TABLE 3

|  | Working Example 1 | Working Example 2 | Working Example 3 | Comparative Example 4 | Comparative Example 5 |
|---|---|---|---|---|---|
| Δf (hy) [Hz] | 200 | 325 | 250 | 40 | 115 |
| Ratio to Comparative Example 1 (%) | 5.00 | 8.13 | 6.25 | 1.00 | 2.88 |

In the working examples 1-3, Δf(hy) increased by five to eight times that in the comparative example 1. Because the increase rate of Δf(hy) is greater than the increase rate of Δf(coa), it was ensured that the probe molecule absorption became more highly dense than the spacer molecule absorption in the working examples 1-3.

In the comparative example 2, the increase rate of Δf(hy) was smaller than that of Δf(coa), and the amount of increase by coabsorption when 1 M of $Na^+$ was added did not produce any effect because the added concentration was 1 M. The QCM measurement data of the working examples 1-3 and comparative examples 1 and 2 are shown in FIGS. 1-5, respectively. It was visually ensured that the absorbed probe molecules became highly dense by addition of the divalent cations, clearly indicating that an addition of a small amount of the divalent cations suppresses the repulsion among the nucleic acids.

What is claimed is:

1. A method of manufacturing a biosensor, comprising:
   applying a solution to an Au solid support, the solution having a plurality of probe molecules, a plurality of spacer molecules, and at least one kind of a divalent cation that includes a $CaCl_2$, each of the plurality of probe molecules including a nucleic acid, each of the plurality of spacer molecules not including a nucleic acid and not covalently linked to the plurality of probe molecules, and the CaCl2 at a total concentration in a range of 0.1 mM-20 mM; and
   adsorbing the plurality of probe molecules and the plurality of spacer molecules onto the Au solid support, a surface concentration of the plurality of probe molecules being at least $1 \times 10^8$ and at most $1 \times 10^{16}$ per square centimeter, and the plurality of spacer molecules being positioned between the plurality of probe molecules.

2. The method according to claim 1, the solution including a monovalent cation at a total concentration in a range of 10 mM-2M.

3. The method according to claim 1, each of the plurality of nucleic acids including a single- or double-stranded oligonucleotide or polynucleotide.

4. The method according to claim 1, the nucleic acid molecule including one of a DNA, a RNA, a peptide nucleic acid, a cyclohexylanyl nucleic acid, a hexytol nucleic acid, a pyranosyl-RINA, an oligonucleotide, and a polynucleotide.

5. The method according to claim 1, each of the plurality of probe molecules having a functional group at an end, the functional group being adapted to be immobilized on the solid support.

6. The method according to claim 1, each of the plurality of spacer molecules being expressed as X-A-B, the X being a functional group that is adapted to be immobilized on the solid support, the A being an alkylene group or a polyethylene glycol group, and the B being one of a hydroxyl group, an amino group, a ferrocenyl group, and a carboxyl group.

7. The method according to claim 1, the solid support having a metal film on a surface, each of the plurality of probe molecules having a thiol group that contacts the metal film, and each of the plurality of spacer molecules having a thiol group that contacts the metal film.

8. The method according to claim 1, the plurality of probe molecules and the plurality of spacer molecules being coadsorbed on the solid support.

9. A method of manufacturing a biosensor, comprising:
   applying a solution to an Au solid support, the solution having a plurality of probe molecules, a plurality of spacer molecules, and at least one kind of divalent cation, each of the plurality of probe molecules including a nucleic acid and one functional group, the one functional group being adapted to be immobilized on the solid support, each of the plurality of spacer molecules being expressed as X-A-B, the X being another functional group that is adapted to be immobilized on the solid support, the A being an alkylene group or a polyethylene glycol group, and the spacer molecule not being covalently linked to the probe molecule and not containing the nucleic acid, and the divalent cation at a total concentration in a range of 0.1 mM-20 mM; and
   adsorbing the plurality of probe molecules and the plurality of spacer molecules onto the Au solid support, a surface concentration of the plurality of probe molecules being at least $1 \times 10^8$ and at most $1 \times 10^{16}$ per square centimeter, and the plurality of spacer molecules being positioned between the plurality of probe molecules.

10. The method according to claim 9, the B being one of a hydroxyl group, amino group, a ferrocenyl group, and a carboxyl group.

11. A method of manufacturing a biosensor, comprising:

applying a solution to an Au solid support, the solution having a plurality of probe molecules, a plurality of spacer molecules, and at least one kind of a divalent cation, each of the plurality of probe molecules including a nucleic acid, each of the plurality of spacer molecules not including a nucleic acid and not covalently linked to the plurality of probe molecules, and the divalent cation at a total concentration in a range of 0.1 mM-20 mM; and adsorbing the plurality of probe molecules and the plurality of spacer molecules onto the Au solid support, the plurality of spacer molecules being positioned between the plurality of probe molecules.

12. The method according to claim 9, the polyethylene molecule also having a thiol group at an end.

13. The method of manufacturing a biosensor according to claim 11, the plurality of probe molecules being configured to hybridize with a plurality of target nucleic acids, the plurality of spacer molecules being configured not to hybridize with the plurality of target nucleic acids.

* * * * *